United States Patent
Sacchetti

(10) Patent No.: US 8,512,300 B1
(45) Date of Patent: Aug. 20, 2013

(54) ENTERAL FEEDING SYSTEM

(75) Inventor: Peter Sacchetti, Attleboro, MA (US)

(73) Assignee: Alcor Scientific, Inc., Smithfield, RI (US)

( * ) Notice: Subject to any disclaimer, the term of this patent is extended or adjusted under 35 U.S.C. 154(b) by 0 days.

(21) Appl. No.: 13/463,911

(22) Filed: May 4, 2012

Related U.S. Application Data

(60) Provisional application No. 61/491,435, filed on May 31, 2011.

(51) Int. Cl.
*A61M 5/00* (2006.01)
*A61M 31/00* (2006.01)
*A47B 85/00* (2006.01)
*A47C 31/00* (2006.01)
*G08B 23/00* (2006.01)

(52) U.S. Cl.
USPC ............... 604/246; 604/516; 5/617; 5/658; 340/573.7

(58) Field of Classification Search
USPC .... 604/48, 516, 246; 340/573.7; 5/625–629, 5/658, 662, 600, 612, 617
See application file for complete search history.

(56) References Cited

U.S. PATENT DOCUMENTS

| | | | |
|---|---|---|---|
| 6,486,792 B1 * | 11/2002 | Moster et al. | 340/4.11 |
| 6,966,086 B2 * | 11/2005 | Metz et al. | 5/510 |
| 2006/0278785 A1 * | 12/2006 | Wiesner et al. | 248/231.71 |
| 2010/0060463 A1 * | 3/2010 | Sacchetti | 340/573.7 |

* cited by examiner

*Primary Examiner* — Bhisma Mehta
*Assistant Examiner* — Lauren M Peng
(74) *Attorney, Agent, or Firm* — Barlow, Josephs & Holmes, Ltd.

(57) ABSTRACT

An enteral feeding system reduces medical risk for aspirational pneumonia when an angle of the head gatch section is outside a predetermined range of 30-45 degrees. The system comprises a hospital bed having a head gatch section and an intravenous pole connected to an enteral feeding pump. The pump has a fluid sensor which operates properly when the pump is positioned along a vertical axis. The pole is connected to the head gatch section at a 30 degree angle offset from a vertical axis. In operation, when the head gatch section is positioned less than 30 degrees, the pump will stop operating and when the head gatch section is positioned at 30 degres, the pump will operate since the pump is positioned along a vertical axis to allow the fluid sensor to detect fluid.

17 Claims, 2 Drawing Sheets

ENTERAL FEEDING SYSTEM

CROSS REFERENCE TO RELATED APPLICATION

This application is related to and claims priority from earlier filed U.S. Provisional Application for Patent Ser. No. 61/491,435 filed May 31, 2011, the entire contents of which are incorporated herein by reference.

BACKGROUND OF THE INVENTION

The present invention generally relates to a enteral feeding system, more specifically, relates to a device, methods and system for a enteral feeding system that triggers an operational response and an alert of a medical risk for aspirational pneumonia when an enteral pump is delivering liquid nutrients to a patient and an angle of the head gatch section is outside a predetermined range.

Enteral feeding is used for patients who are unable to eat normally. An enteral feeding pump is typically used to pump liquid nutrient directly into the gastro-intestinal tract from a source container. While the use of an enteral feeding pump is a common device for delivering a liquid nutrient to a patient, complications can arise during the feeding.

In particular, one of these complications is aspirational pneumonia. Typically, aspirational pneumonia occurs when a patient's bed is positioned at an angle sufficient to allow the patient's gastric fluids to ascend the esophagus and be inhaled into the lungs. When the bed angle reaches this point, the stomach contents are able to percolate up through the esophagus and down into the lungs. When the enteral feeding pump continues to deliver liquid nutrients, despite the undesired low bed angle, it increases the medical risk of aspirational pneumonia.

Current practice utilizes an "IV pole" which is a free-standing pole to which the enteral pump is attached at about midlength and from which a bag or bottle container is hung from the top-mounted hook. Tubing from the container is routed through the pump and connected to the patient being fed. Many patients who are fed this way receive the liquid nutrition while lying in a bed.

A popular bed type, for patients requiring this feeding method, is a "hospital" bed which has the feature which allows the head end of the bed to be elevated. It is commonly recommended that while patients are receiving liquid nutrient, the head or gatch of the bed is elevated, usually to an angle of 30-45 degrees. The purpose of this is to prevent the reverse flow of liquid nutrient from the stomach, up the esophagus, and then potentially into the trachia. This can lead to respiratory distress and possibly aspiration pneumonia. This is a well known problem and has been the subject of several scientific publications.

From the literature, it is clear that the procedure to elevate the bed is not always followed in all patient settings. It is also clear that the occurrence of aspiration events associated with enteral feeding are greatly underreported due to its lack of obvious immediate effects, especially in patients who lack cognition.

Therefore, there remains a need in the prior art for an enteral feeding system that reduces the risk of aspirational pneumonia.

BRIEF SUMMARY OF THE INVENTION

The invention preserves the advantages of prior enteral feeding systems. In addition, it provides new advantages not found in currently available enteral feeding systems and overcomes many disadvantages of such currently available enteral feeding systems. The invention provides an enteral feeding system that reduces the medical risk for aspirational pneumonia when an enteral pump is delivering liquid nutrients to a patient and an angle of the head gatch section is outside a predetermined range of 30-45 degrees.

The enteral feeding system reduces medical risk for aspirational pneumonia when an angle of the head gatch section is outside a predetermined range of 30-45 degrees. The system comprises a hospital bed having a head gatch section and an intravenous pole connected to an enteral feeding pump. The pump has a fluid sensor which operates properly when the pump is positioned along a vertical axis. The pole is connected to the head gatch section at an angle offset from a vertical axis from a range of 30-45 degrees, preferably 30 degrees. In operation, when the head gatch section is positioned outside a range of 30-45 degrees, or less than 30 degrees, the pump will stop operating. When the head gatch section is positioned within a range of 30-45 degrees, or 30 degrees, the pump will operate since the pump is positioned along a vertical axis or substantially vertical axis to allow the fluid sensor to detect fluid.

The present invention also includes a method for reducing the medical risk of aspirational pneumonia using a hospital bed, intravenous pole, and an enteral feeding pump. First, an intravenous pole is connected to an adjustable head gatch section of the hospital bed at an angle offset from a vertical axis from a range of 30-45 degrees, preferably 30 degrees. Second, the enteral feeding pump is removably connected to a surface of the intravenous pole. Third, the operation of the enteral feeding pump having one or more fluid sensors is enabled to pump nutrient liquid through a feeding set. If the head gatch section is elevated to 30 degrees, or possibly a range of 30-45 degrees during operation of the enteral feeding pump, the fluid sensor will properly detect the flow of fluid to maintain the operation of the feeding pump. If the head gatch section is lowered to a range less than 30 degrees, the fluid sensor will not detect the flow of fluid which results in the stopping of the operation of the enteral feeding pump. In operation, when the head gatch section is positioned less than 30 degrees, the enteral feeding pump will stop operating and when the head gatch section is positioned within a range of 30-45 degrees, or 30 degrees, the enteral feeding pump will operate since the pump is now positioned along a vertical axis to allow the fluid sensor to detect fluid.

It is therefore an object to reduce the medical risk for aspirational pneumonia.

It is another object to control the operation of a pump when a patient has a medical risk for aspirational pneumonia.

A further object is to deliver nutrients to a patient when the head gatch section is within a range of 30-45 degrees to reduce the risk of aspirational pneumonia.

Another object is to provide a safe and effective way for feeding patients using an enteral pump.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENTS

Figure 1:
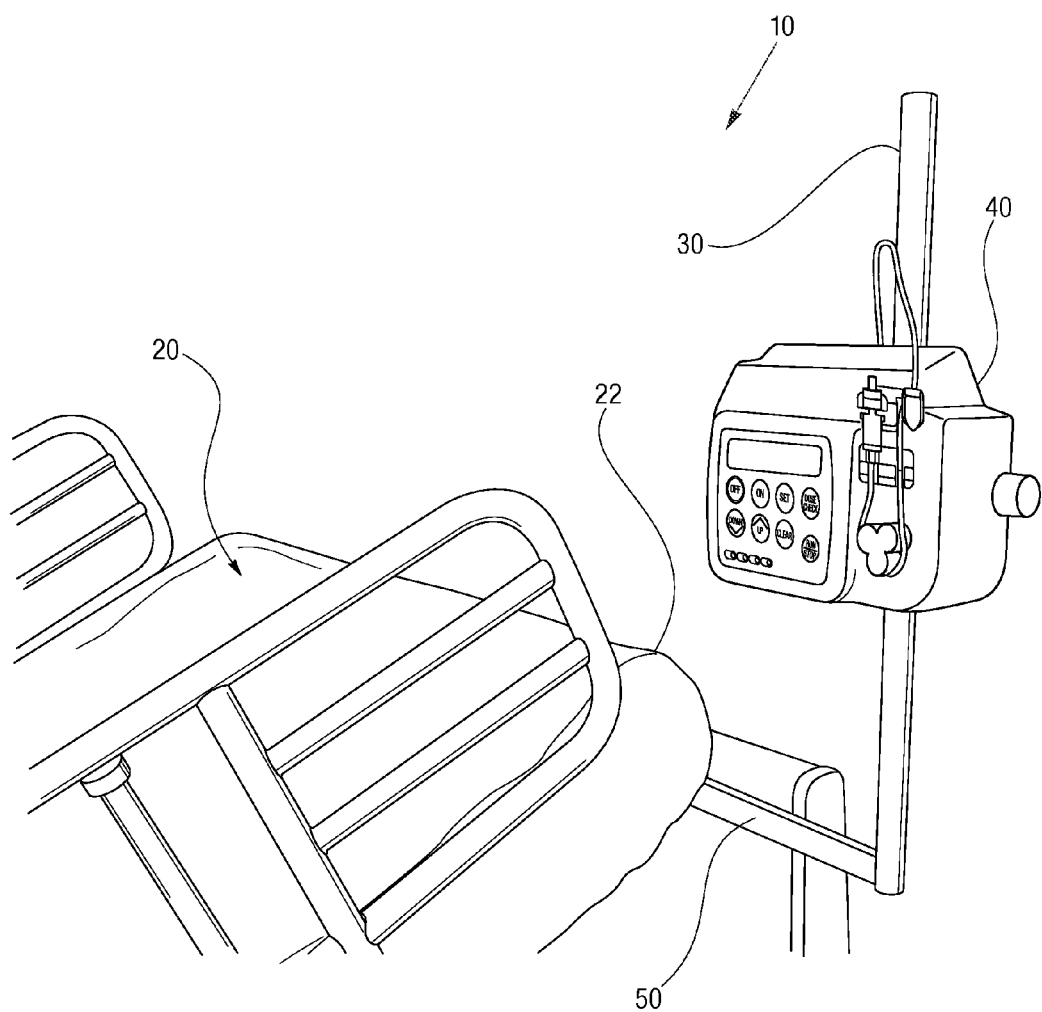
FIG. 1 is a perspective view of the enteral feeding system of the present invention with the head gatch in an elevated position and the pump positioned along a substantially vertical axis.
Figure 2:
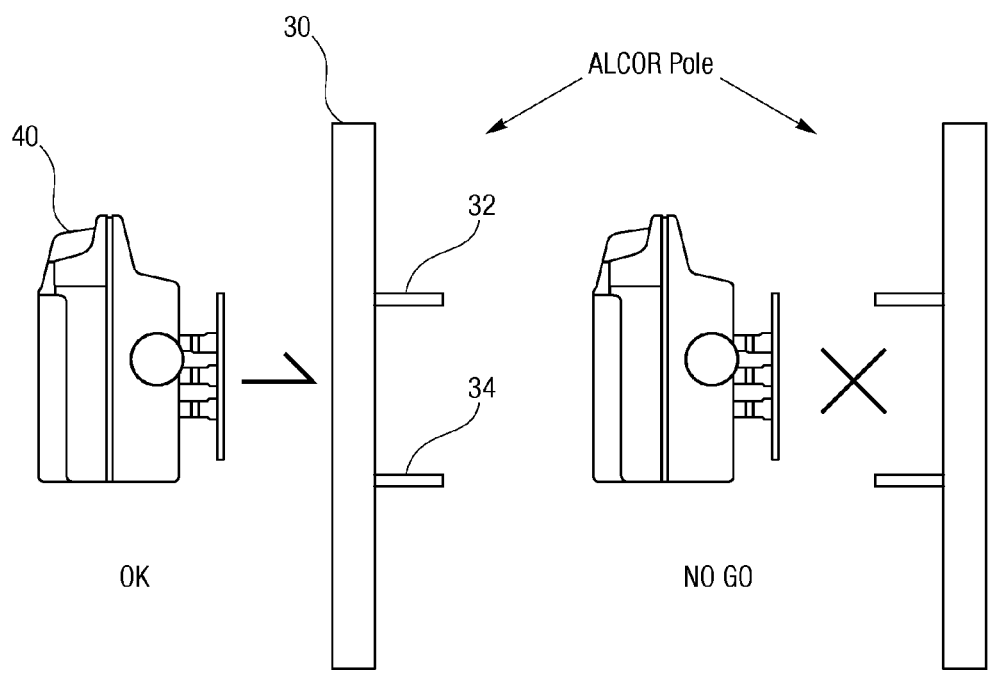
FIG. 2 is a top and side view of the intravenous pole with horizontal rods for signaling proper orientation of the enteral feeding pump.
Figure 2:
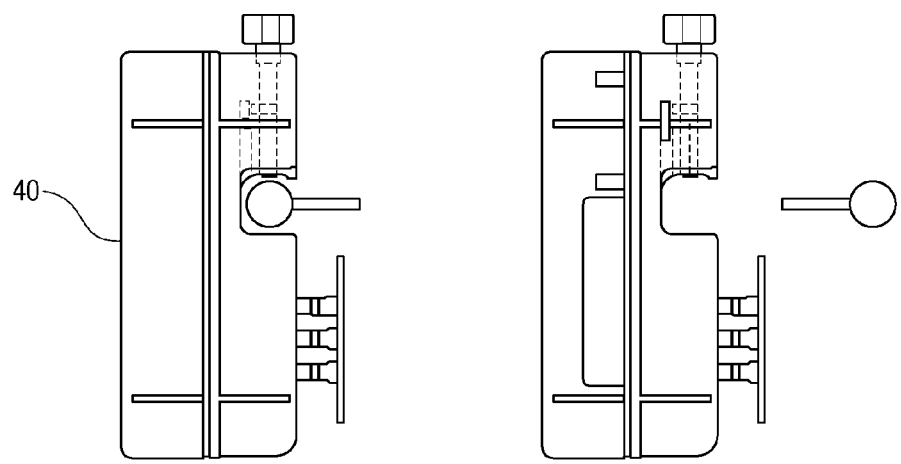

In accordance with the invention of FIGS. 1-2, the invention generally relates to a enteral feeding system 10, more specifically, relates to a device, methods and systems for an enteral feeding system 10 that reduces the medical risk for aspirational pneumonia when an enteral pump 40 or enteral pump assembly is delivering liquid nutrients to a patient and an angle of the head gatch section 22 of a hospital bed 20 is outside a predetermined range of 30-45 degrees.

The enteral feeding system 10 reduces medical risk for aspirational pneumonia when an angle of the head gatch section 22 is outside a predetermined range of 30-45 degrees or less than 30 degrees. The system comprises a hospital bed 20 having a head gatch section 22 or moveable head end of the hospital or patient bed 20, an intravenous pole 30 connected to the head gatch section 22, and an enteral feeding pump 40, such as a Sentinel Enteral Feeding Pump, connected to the intravenous pole 30. Of course, the enteral feeding system 10 may also include an intravenous bag (not shown) connected to the intravenous pole 30 and a delivery set connected to the enteral feeding pump 40. A pole clamp, integrated within the feeding pump 40, may be used to removably connect the enteral feeding pump 40 to the intravenous pole 30. The pump 40 has a fluid sensor or drop detection sensor that is sensitive to vertical angular position perpendicular to the frontal axis. The fluid sensor or drop detection sensor operates properly when the pump 40 is positioned substantially along a vertical axis.

The intravenous pole 40 is connected to the head gatch section 22 at an angle offset from a vertical axis from a range of 30-45 degrees, preferably 30 degrees. Of course, it is contemplated that the intravenous pole 30 may be connected at an angle offset from a vertical axis from a range other than 30-45 degrees depending upon the configuration of the head gatch section 22, hospital bed 20, pump 40, and the intravenous pole 30. The pole 30 is designed so that, when the head gatch section 22 is horizontal or in a lowered position, the pole 30, and therefore the pump 40, is at an angle range of 30 degrees off the vertical axis. When the head gatch section 22 of the bed 20 is raised to 30 degrees elevation, the pump 40 is positioned along a vertical or substantially vertical axis.

In one embodiment, the offset angle of the pole 30 relative to the vertical axis is within a range of 30-45 degrees and correlates to the degrees by which the head gatch section 22 is elevated or raised to operate or stop the enteral feeding pump 40. For example, if the angle offset of the pole 30 is 30 degrees then the head gatch section 22 needs to be raised 30 degrees for the pump 40 to operate properly along a vertical axis or substantially vertical axis. Another example, if the angle offset of the pole 30 is 45 degrees, then the head gatch section 22 needs to be raised 45 degrees for the pump 40 to operate properly along a vertical axis. It should be noted that the intravenous pole 30 is an example and that another type of pole or support may be used to connect the pump 40 to the head gatch section 22 of the hospital bed 20.

In one embodiment, the vertical axis is approximately 90 degrees. The substantially vertical axis may range plus or minus 15 degrees from 90 degrees. However, it is contemplated that the vertical axis could be greater than or less than 90 degrees depending upon the configuration of the head gatch section 22, hospital bed 20, pole 30, offset angle of the pole 30, and pump 40. It should be noted that the pump 40 may operate when positioned along vertical axis or a substantially vertical axis depending upon the configuration of the pump and its tolerance for operation, specifically the fluid sensor, outside the preferred vertical axis position.

The intravenous pole 30 includes one or more horizontal rods 32, 34 extending along a horizontal axis from a surface of the pole 30 to facilitate proper orientation of an enteral feeding pump 40 relative to the hospital bed 20. The enteral feeding pump 40 is connected to the intravenous pole 30 on surface of pole 30 opposite the rods 32, 34 to orient the enteral feeding pump 40 towards a foot end section of a hospital bed 20. The pole 30 also has a feature which only allows the pump 40 to be mounted in one rotational orientation such that the front of the pump 40 must be perpendicular to the tilt axis and faces the foot end section of the bed 20. This insures that the drops falling through the sensor beam are on the angle-dependent axis for blocking or not blocking the beam with the enteral pump 40.

In operation, when the head gatch section 20 is positioned less than 30 degrees, the pump 40 will stop operating and when the head gatch section 22 is positioned at 30 degrees, the pump 40 will operate since the pump 40 is positioned along a vertical axis or substantially vertical axis to allow the fluid sensor to detect fluid. In operation, a caregiver may initiate enteral feeding with the head gatch section 22 of the hospital bed 20 at any elevation. However, if the elevation of the head gatch section 22 is less than 30 degrees, and assuming the offset angle of the pole is 30 degrees, the tilted pump drip chamber will cause drops of liquid nutrient to fall in a way that they do not block or intercept the sensor light beam of the fluid sensor. When this occurs, the pump stops and alarms. In one embodiment, the alarm signals visually and audibly. This prevents feeding the patient at a low elevation which therefore helps prevent liquid aspiration. In one embodiment, the head gatch section 20 must be elevated to at least 30 degrees for the pump 40 to be correspondingly be elevated to the vertical position along a vertical axis. At this elevation, the pump 40 will operate without alarming.

In one embodiment, a support arm member 50 is connected to the head gatch section 22 of the hospital bed 20 and to the intravenous pole 30. A proximal end of the support arm member 50 is connected to the head gatch section 22 and the distal end of the support arm member 50 is connected to the intravenous pole 30. The support arm member 50 is removably connected to the head gatch section 22. Alternatively, the support arm member 50 is attached to the head gatch section 22. The support arm member 50 may connect or attach to a frame or deck of the head gatch section 22 so long as the support arm member 50 moves relative to the head gatch section 22. In one embodiment, the support arm member 50 is perpendicular relative to the intravenous pole 30. The support arm member 50 may extend along a horizontal axis parallel to a horizontal axis of a top portion of the head gatch section 22. The support arm member 50 may extend outwardly from the head gatch section to facilitate operation and viewing. In another embodiment, the distal end of the support arm member 50 is received within a slot defined within a bottom portion of the intravenous pole 30.

The present invention also includes a method for reducing the medical risk of aspirational pneumonia using a hospital bed, intravenous pole 30, and an enteral feeding pump 40. First, an intravenous pole 30 is connected to an adjustable head gatch section 22 of the hospital bed 20 at an angle offset from a vertical axis from a range of 30-45 degrees, preferably 30 degrees. Second, the enteral feeding pump 40 is removably connected to a surface of the intravenous pole 30. Third, the operation of the enteral feeding pump 40 having one or more fluid sensors is enabled to pump nutrient liquid through a feeding set. If the head gatch section 22 is elevated to at least 30 degrees during operation of the enteral feeding pump 40, the fluid sensor will properly detect the flow of fluid to maintain the operation of the feeding pump 40. If the head gatch section 22 is lowered to a range less than 30 degrees, the fluid sensor will not detect the flow of fluid which results in the stopping of the operation of the enteral feeding pump 40.

In operation, when the head gatch section 22 is positioned less than 30 degrees, the enteral feeding pump 40 will stop operating and when the head gatch section 22 is positioned above 30 degrees, the enteral feeding pump 40 will operate since the pump 40 is now positioned along a vertical axis to allow the fluid sensor to detect fluid.

In view of the foregoing, a new and novel head gatch alarm system 10 is provided that reduces medical risk for aspirational pneumonia and an operational response when an enteral pump 40 is delivering liquid nutrients to a patient and an angle of the head gatch section is below or outside a predetermined range of 30-45 degrees.

It would be appreciated by those skilled in the art that various changes and modifications can be made to the illustrated embodiments without departing from the spirit of the present invention. All such modifications and changes are intended to be within the scope of the present invention.

What is claimed is:

1. A hospital bed, comprising:
   an adjustable head gatch section, the adjustable head gatch section configured to provide a range of movement between a raised position and a lowered position;
   pole member attached to the adjustable head gatch section;
   an enteral feeding pump connected to the pole member to share a common axis, said enteral feeding pump operates when the enteral feeding pump is substantially positioned along a vertical axis,
   whereby when the head gatch section is at or near the lowered position, the enteral feeding pump will stop operating; and when the head gatch section is at or near the raised position, the enteral feeding pump will operate since the pump is substantially positioned along the vertical axis to detect fluid.

2. The hospital bed of claim 1, wherein said pole member includes one or more rods extending along a horizontal axis from the pole member to facilitate proper orientation of the enteral feeding pump relative to the hospital bed.

3. The hospital bed of claim 2, wherein the enteral feeding pump is connected to the pole member on a surface of pole member opposite the rods to orient the enteral feeding pump towards a foot end section of the hospital bed.

4. The hospital bed of claim 1, wherein said pole member is attached to the head gatch section at an angle about 30 degrees offset from the vertical axis.

5. The hospital bed of claim 1, wherein said pole member is attached to the head gatch section at an angle ranging from 20 degrees to 45 degrees offset from the vertical axis.

6. The hospital bed of claim 1, wherein said pole member is attached to the head gatch section at an angle ranging from 20 degrees to 35 degrees offset from the vertical axis.

7. The hospital bed of claim 1, wherein said pole member is connected to the head gatch section at an angle ranging from 0 degrees to 45 degrees offset from the vertical axis.

8. The hospital bed of claim 1, wherein the pole member is fixedly attached to the adjustable head gatch section.

9. The hospital bed of claim 1, further comprising:
   a support arm member connected to the head gatch section of the hospital bed, the support arm member connected to the pole member.

10. The hospital bed of claim 9, wherein the support arm member is removably connected to the head gatch section.

11. The hospital bed of claim 10, wherein the support arm member is perpendicular relative to the pole member.

12. The hospital bed of claim 11, wherein the support arm member extends along a horizontal axis parallel to a horizontal axis of a top portion of the head gatch section.

13. The hospital bed of claim 12, wherein a proximal end of the support arm member is connected to the head gatch section and the distal end of the support arm member is connected to the pole member.

14. The hospital bed of claim 13, wherein the support arm member extends outwardly from the head gatch section to facilitate operation.

15. The hospital bed of claim 14, wherein the distal end of the support arm member is received within a slot defined within a bottom portion of the pole member.

16. The hospital bed of claim 1, further comprising:
   a pole clamp removably connecting the enteral feeding pump to the pole member.

17. The hospital bed of claim 1, further comprising:
   an intravenous bag connected to the pole member;
   and a delivery set connected to the enteral feeding pump.

* * * * *